(12) United States Patent
Li

(10) Patent No.: US 10,588,864 B2
(45) Date of Patent: Mar. 17, 2020

(54) PHARMACEUTICAL COMPOSITIONS FOR COLON-SPECIFIC DELIVERY

(71) Applicant: Gateway Pharmaceutical LLC, Chesterfield, MO (US)

(72) Inventor: Lianli Li, Chesterfield, MO (US)

(73) Assignee: Gateway Pharmaceuticals LLC, Chesterfiled, MO (US)

( * ) Notice: Subject to any disclaimer, the term of this patent is extended or adjusted under 35 U.S.C. 154(b) by 86 days.

(21) Appl. No.: 15/703,172

(22) Filed: Sep. 13, 2017

(65) Prior Publication Data
US 2018/0000740 A1 Jan. 4, 2018

Related U.S. Application Data

(63) Continuation-in-part of application No. 15/379,371, filed on Dec. 14, 2016, now abandoned.

(60) Provisional application No. 62/307,407, filed on Mar. 11, 2016.

(51) Int. Cl.
| | |
|---|---|
| *A61K 9/48* | (2006.01) |
| *A61K 9/20* | (2006.01) |
| *A61K 9/28* | (2006.01) |
| *A61K 31/4164* | (2006.01) |
| *A61K 9/00* | (2006.01) |

(52) U.S. Cl.
CPC .......... *A61K 9/4808* (2013.01); *A61K 9/0053* (2013.01); *A61K 9/205* (2013.01); *A61K 9/2081* (2013.01); *A61K 9/286* (2013.01); *A61K 9/2846* (2013.01); *A61K 9/4816* (2013.01); *A61K 9/4825* (2013.01); *A61K 9/4866* (2013.01); *A61K 9/4891* (2013.01); *A61K 31/4164* (2013.01); *A61K 9/2018* (2013.01); *A61K 9/2027* (2013.01); *A61K 9/2054* (2013.01)

(58) Field of Classification Search
CPC .. A61K 9/5036; A61K 9/2081; A61K 9/0053; A61K 9/2846; A61K 9/205
See application file for complete search history.

(56) References Cited

U.S. PATENT DOCUMENTS

| | | | |
|---|---|---|---|
| 5,914,132 A | 6/1999 | Kelm | |
| 6,224,910 B1 | 5/2001 | Ullah | |
| 6,228,396 B1 | 5/2001 | Watts | |
| 7,871,643 B2 * | 1/2011 | Lizio | A61K 9/5015 424/452 |
| 9,023,368 B2 | 5/2015 | Basit | |
| 9,192,583 B2 | 11/2015 | Shah | |
| 9,237,760 B2 | 1/2016 | Ravishankar | |
| 2006/0057204 A1 | 3/2006 | Penhasi | |
| 2006/0240123 A1 | 10/2006 | Armstrong | |
| 2007/0026082 A1 | 2/2007 | Lizio | |
| 2013/0259947 A1 | 10/2013 | Padhi | |

FOREIGN PATENT DOCUMENTS

| | | |
|---|---|---|
| EP | 2046304 B1 | 10/2013 |
| WO | 2012075015 A2 | 6/2012 |
| WO | 2012075015 A3 | 6/2012 |
| WO | 2015089326 A1 | 6/2015 |
| WO | 2015089326 A9 | 6/2015 |
| WO | 2015089335 | 6/2015 |

OTHER PUBLICATIONS

Clinical Trial NCT02200328, downloaded from https://clinicaltrials.gov/archive/NCT02200328/2014_07_24, Jan. 10, 2018 (Year: 2014).*
Amidon, S. , et.al. "Colon-Targeted Oral Drug Delivery Systems: Design Trends and Approaches", AAPS PharmSciTech, vol. 16, Issue 4, pp. 731-741.
Auriemma, G., et al, Prilling for the development of multi-particulate colon drug delivery systems: Pectin vs. pectin-alginate beads, Carbohydrate Polymers, 2013, 92, 367-373.
EMC Patient Information Leaflet, "Metronidazole Tablets" (2012), accessed at https://www.medicines.org.uk/emc/medicine/18111, Jul. 25, 2017.
Flint, H.J., et al., Microbial degradation of complex carbohydrates in the gut, Gut Microbes, 2012, 3, 289-306.
Gauri, B., et al., Formulation and evaluation of colon targeted oral drug delivery systems for metronidazole in treatment of amoebiasis, International Journal of Pharma and Bio Sciences, 2011, 2, 528-538.
Google Patent Translation, Lizio et al., EP2046304 B1, accessed Jul. 26, 2017.
International Search Report and Written Opinion for PCT Application No. PCT/US2017/021492, dated Jun. 7, 2017, filed on Mar. 9, 2017, 11 pages.
Ji, et al., Journal of Drug Targeting, 15:123-131 (2007).
Kumar, P. et al. Colon Targeted Delivery Systems of Metronidazole Based on Osmotic Technology: Development and Evaluation. Chem. Pharm. Bull. 56(9) 1234-1242 (2008).
Kumar, R. et al., Polysaccharides Based Colon Specific Drug delivery: A Review Int. J. PharmTech Res., 2008, 1, 334-346.

(Continued)

*Primary Examiner* — Kyle A Purdy
(74) *Attorney, Agent, or Firm* — Florek & Endres PLLC

(57) ABSTRACT

Disclosed are pharmaceutical particulates which release a pharmaceutical compound into the colon following oral administration. A particulate comprises a core comprising a pharmaceutical compound, an inner coating surrounding the core, wherein the inner coating comprises a pharmaceutically acceptable polysaccharide that is susceptible to enzymatic digestion by one or more enzymes present colonic microflora, and an outer coating surrounding the inner coating, wherein the outer coating comprises a polymer which is stable at upper gastrointestinal pH but can dissolve at pH>6. The core of a particulate can further comprise an excipient such as a diluent, a binder, a disintegrant, a lubricant, a glidant or a combination thereof. Particulates can comprise pharmaceutical compounds for treating colonic diseases such as *C. difficile* infection, ulcerative colitis, colon cancer, and Crohn's disease.

17 Claims, 6 Drawing Sheets

(56) References Cited

OTHER PUBLICATIONS

Maestrolli, F., et al., Development of enteric-coated calcium pectinate microspheres intended for colonic drug delivery. European Journal of Pharmaceutics and Biopharmaceutics, 2008, 69, 508-518.

Matweb, "Evonik EUDRAGIT FS 30 D Copolymer", accessed at http://matweb.com/earch/datasheettext.aspx?matguid=5b05a98a18a048af950eec53132032e2, Jul. 25, 2017.

Milojevic, S. et al., Amylose as a coating for drug delivery to the colon: Preparation and in vitro evaluation using 5-aminosalicylic acid pellets, J. Controlled Release, 1996, 38, 75-94.

Mura, P., et al., Development of Enteric-coated Pectin-based Matrix Tablets for Colonic Delivery of Theophylline. Journal of Drug Targeting, 2003, 11 (6), pp. 365-371.

Newton, A.M.J., et al., Pectin-HPMC E15LV Vs pH sensitive polymer coating films for delayed drug delivery to the colon: a comparison of two dissolution models to assess colonic targeting performance in-vitro., Int. J. Appl. Res. Nat. Prod., 2012, 5, 1-16.

Nugent, S.G., et al., Intestinal luminal pH in inflammatory bowel disease: possible determinants and implications for therapy with aminosalicylates and other drugs, Gut 48, 571-577, 2001.

Pradeep, B.V., et al., Development of enteric coated pectin coated matrix tablets of metronidazole for colon targeting. IJPRD, 2011, 3, 10-16.

Vaidya et.al. "Metronidazole loaded pectin microspheres for colon targeting", Journal of Phrmaceutical Sciences, vol. 98, No. 11, pp. 4229-4236; Nov. 30, 2009 (Nov. 30, 2009) abstract, p. 4230, pp. 4233-4235, Fig.4.

Varshosaz, J., Pectin Film Coated Pellets for Colon-targeted Delivery of Budesonide: In-vitro/In-vivo Evaluation in Induced Ulcerative Colitis in Rat., Iranian Journal of Pharmaceutical Research, 2012, 11, 733-745.

Kumar, T. et al., Natural Excipients: A Review, Asian Journal of Pharmacy and Life Science 2(1), 97-108, 2012.

International Application No. PCT/US2017/021492; International Preliminary Report on Patentability, dated Sep. 20, 2018; 8 pages.

Vaidya A et al., Pectin—metronidazole prodrug bearing microspheres for colon targeting, Journal of Saudi Chemical Society, vol. 19, Issue 3, May 2015, pp. 257-264.

* cited by examiner

PHARMACEUTICAL COMPOSITIONS FOR COLON-SPECIFIC DELIVERY

Pharmaceutical treatment of colon diseases, such as *C. difficile* infection, ulcerative colitis, and Crohn's disease, requires that the drug reach the colon in an effective form. Current pharmaceutical treatments include oral dosage forms and injections, however, these forms of dosage administration have several disadvantages relative to the present teachings. Non-targeted dosage forms frequently have side effects on the whole body. Additionally, non-targeted dosage forms may not effectively reach the infected location because they are released throughout the gastrointestinal tract.

Consequently, many different groups have attempted to develop formulations that target the colon. The majority of formulations include pH-dependent coatings. The jejunum of the small intestine can have a luminal pH of 5.0-6.0 and the ileum of the small intestine can have a luminal pH from 6.0-7.5 (Kumar, R. et al., *Int. J. PharmTech Res.*, 2008, 1, 334-346). Colon luminal pH can range from 6.0-7.6 (Kumar, R. et al., *Int. J. PharmTech Res.*, 2008, 1, 334-346). Since the distal side of the small intestine can have a pH similar to that of the colon, existing formulations with pH-dependent coatings do not dissolve primarily at the colon.

U.S. Pat. No. 9,192,583 to Shah et al. discloses a multiparticulate formulation for a volatile terpene-based active ingredient. A particulate of this disclosure includes a solid core containing the terpene-based active ingredient and a microcellulose excipient, a continuous proteinaceous subcoating over the core, and an enteric coating over the subcoating. This patent does not disclose the use of pectin or other polysaccharides. Additionally, the multiparticulate taught in this patent releases 50% of its terpene-based active ingredient in 1 hour with total release over 8 hours.

U.S. Pat. No. 6,224,910, to Ullah et al. teaches a dosage form with a polymethacrylate coating such as a EUDRAGIT® L (Evonik Corporation, Parsippany, N.J.) and an optional top coating of an anti-adherent, which can be hydrophobic material such as talc, magnesium stearate or fumed silica. This formulation is stable at pH 3, but releases at pH 4.5. This patent does not disclose the use of pectin or other polysaccharides.

U.S. Pat. No. 5,914,132 to Kelm et al. teaches a pharmaceutical dosage form with two pH dependent polymer coatings. This patent does not disclose the use of pectin or other polysaccharides.

Polysaccharides are used in formulations intended to target drugs to the colon. However, such formulations are slow-release formulas that do not provide drug release concentrated at the colon.

U.S. Pat. No. 9,237,760 to Ravishankar et al. discloses a pharmaceutical or neutraceutical core, surrounded by two controlling layers. The inner controlling layer surrounds the core and comprises cationic copolymers and anionic copolymers; the outer controlling layer comprises anionic copolymers. However, this patent does not disclose separate layers for copolymers and polysaccharides, nor does it disclose pectin. This patent also discloses an extended release formulation: complete release is described as occurring in "8 hours or less".

Newton, A. M. J., et al. (*Int. J. Appl. Res. Nat. Prod.*, 2012, 5, 1-16) compared the dissolution of mesalamine tablets that were coated with either a mixture of pectin and hydroxypropylmethylcellulose (HPMC) or EUDRAGIT® L100 polymethacrylate (Evonik Corporation, Parsippany, N.J.) to form a slow release formulation. This reference does not disclose a dosage form coated with both pectin and a polymethacrylate.

Auriemma, G., et al (*Carbohydrate Polymers*, 2013, 92, 367-373) describes a multiparticulate drug delivery system produced by a prilling technique in combination with an enteric coating. This reference describes a formulation of an active drug (piroxicam) mixed with a $Zn^+$-pectin, and EUDRAGIT® S100 polymethacrylate coating. However, this reference does not disclose using pectin as part of a coating of a microparticulate. This reference also discloses approximately 50-65% of drug release in simulated gastric fluid for their formulation.

U.S. Pat. No. 9,023,368 to Basit et al. describes a slow release enteric coating that is a mixture of high polysaccharide starches (amylose, amylopectin) and polymers such as EUDARIGIT® S polymethacrylate, but explicitly excludes multi-layer dosage forms.

Milojevic, S. et al. (*J. Controlled Release*, 1996, 38, 75-94) describes layered coatings of glassy amylose with non-pH dependent polymer EUDRAGIT® RS/RL 30D polymethacrylate dispersions in various formulations (plasticized with PEG 300), but were unable to achieve colon-targeted delivery using such formulations. Consequently, this reference recommends mixtures that include ETHOCEL® ethylcellulose (The Dow Chemical Company, Midland, Mich.).

U.S. Pat. No. 6,228,396 to Watts describes a starch capsule intended for targeted release of a drug in the colon. The capsule has a coating of a copolymer of methacrylic acid and methyl methacrylic that dissolves at a pH of 5 or higher. While this patent discloses particulates such as mini-tablets for use in filling a starch capsule, it does not disclose the application of a pH-dependent coating directly to a particulate. This patent discloses polysaccharides including pectin as potential capsule-coating materials that promote release in the colon, but does not describe a particulate comprising pectin or a particulate having a pH-dependent outer coating. Furthermore, the formulation also serves as a slow release formulation: the drug in a capsule described in the patent is not released for over an hour after transfer to a neutral pH buffer.

There is thus an unmet need for a pharmaceutical formulation which, following oral administration, rapidly releases a pharmaceutical compound upon reaching the colon.

SUMMARY

The present inventor has developed drug delivery systems which include oral compositions that can be used to target drugs to the colon, and methods of administering these compositions. In various embodiments, the pharmaceutical composition comprises particulates comprising a) a core comprising an active pharmaceutical compound or salt thereof, b) an inner coating surrounding the core, and c) an outer coating which surrounds the inner coating.

In an embodiment, said particulates comprise:
i. a core comprising metronidazole and one or more pharmaceutically acceptable excipients;
ii. an inner coating surrounding the core comprising a polysaccharide enzyme substrate polymer which is dissolved by enzymes in the colon; and
iii. an outer coating surrounding the inner coating comprising a polymethacrylate which dissolves at pH≥6.

In an embodiment, said core is formulated for immediate release.

In an embodiment, said core dissolves in aqueous media in less than about 60 minutes.

In an embodiment, said dissolution of the core is independent of pH.

In an embodiment, said particulates have a distribution of particle sizes in a range of about 1 mm to about 3 mm.

In an embodiment, said one or more pharmaceutically acceptable excipients is selected from the group consisting of a diluent, a binder, a disintegrant, a lubricant, a glidant and a combination thereof.

In an embodiment, said polysaccharide enzyme substrate polymer is selected from the group consisting of a pectin, xantham gum, locust bean gum, alginate, carrageenan, amylose, guar gum, inulin, dextran, chitosan, chondroitin sulfate and combinations thereof.

In an embodiment, said polysaccharide enzyme substrate polymer is a pectinase substrate.

In an embodiment, said pectinase substrate is a pectin.

In an embodiment, said polymethacrylate is selected from the group consisting of poly(methyl acrylate-co-methyl methacrylate-co-methacrylic acid) 7:3:1, poly(methacrylic acid-co-methyl methacrylate) 1:1, poly(methacrylic acid-co-methyl methacrylate) 1:2, poly(methacrylic acid-co-ethyl acrylate) 1:1, and a combination thereof.

In an embodiment, said polymethacrylate is poly(methyl acrylate-co-methyl methacrylate-co-methacrylic acid) 7:3:1.

In an embodiment, said pharmaceutical composition is a plurality of said particulates in a capsule.

Further disclosed herein is a tablet pharmaceutical dosage form comprising:
 a. a plurality of particulates; and
 b. additional excipients selected from the group consisting of a binder, a colorant, a disintegrant, a lubricant, a glidant, a flavoring, a preservative, a diluent and a combination thereof.

In an embodiment, the total amount of metronidazole in the composition is from 50-800 mg.

In an embodiment, the total amount of metronidazole in the composition is from 250-500 mg.

In an embodiment, the total amount of metronidazole in the composition is 250 mg.

In an embodiment, the total amount of metronidazole in the composition is 500 mg.

Further disclosed is a pharmaceutical composition comprising particulates comprising:
 i. a core comprising metronidazole and one or more pharmaceutically acceptable excipients;
 ii. an inner coating surrounding the core comprising a pectin which is dissolved by enzymes in the colon; and
 iii. an outer coating surrounding the inner coating comprising poly(methyl acrylate-co-methyl methacrylate-co-methacrylic acid) 7:3:1 which dissolves at pH≥7.

Further disclosed is a pharmaceutical composition comprising particulates comprising:
 i. a core comprising metronidazole and one or more pharmaceutically acceptable excipients;
 ii. an inner coating surrounding the core comprising a pectin which is dissolved by enzymes in the colon; and
 iii. an outer coating surrounding the inner coating comprising poly(methacrylic acid-co-methyl methacrylate) 1:1 which dissolves at pH≥6.

In an embodiment, said pharmaceutical composition comprises particulates comprising:
 a. a core comprising metronidazole and one or more pharmaceutically acceptable excipients;
 b. an inner coating surrounding the core comprising a polysaccharide enzyme substrate polymer which is dissolved by enzymes in the colon; and
 c. an outer coating surrounding the inner coating comprising a polymethacrylate which dissolves at pH≥7;
 wherein the combination of said inner and outer coatings changes the dissolution pH of the outer coating to about 0.5 pH higher than the outer coating alone.

In an embodiment, said pharmaceutical composition comprises particulates comprising:
 a. a core comprising metronidazole and one or more pharmaceutically acceptable excipients;
 b. an inner coating surrounding the core comprising a polysaccharide enzyme substrate polymer which is dissolved by enzymes in the colon; and
 c. an outer coating surrounding the inner coating comprising a polymethacrylate which dissolves at pH≥6;
 wherein the combination of said inner and outer coatings changes the dissolution pH of the outer coating to about 0.5 pH higher than the outer coating alone.

In another embodiment, there is provided a method of treating infections of the colon comprising administration of said pharmaceutical dosage form to a patient in need thereof.

In another embodiment, there is provided a method of treating a colon disease comprising administering to a subject in need thereof said pharmaceutical dosage form.

In an embodiment, said colon disease is chosen from colon cancer and an inflammatory bowel disease.

In an embodiment, said inflammatory bowel disease is chosen from *C. difficile* infection, ulcerative colitis, *C. difficile* associated diarrhea, or Crohn's disease.

In an embodiment, said inflammatory bowel disease is *C. difficile* infection.

In an embodiment, said administration is for at least 7 days.

In an embodiment, said administration is for 10-14 days.

In an embodiment, said colon disease is colon cancer.

In an embodiment, the single dose AUC is less than 50% compared to Flagyl® (250 and 500 mg immediate release tablets).

In some embodiments, said one or more pharmaceutically acceptable excipients is chosen from microcrystalline cellulose, a polyvinylpyrrolidone, a sodium starch glycolate, a lactose monohydrate, a cross-linked polyvinyl N-pyrrolidone, a hydroxypropyl cellulose, a hydroxypropylmethylcellulose, a croscarmellose sodium, a crospovidone, silicon dioxide, magnesium stearate or a combination thereof.

In an embodiment, said particulates further comprise a non-functional coating.

In an embodiment, said non-functional coating is chosen from HPMC-based coatings, Opadry or Spectrablend, for separation purpose or cosmetic purpose to add a finish or color to the particulates.

In various configurations, an inner coating can comprise, consist essentially of, or consist of at least one pharmaceutically acceptable polysaccharide that is subject to enzymatic digestion by one or more enzymes present in colonic microflora such as colonic bacteria (see, e.g., Flint, H. J., et al., *Gut Microbes* 3:4, 289-306, 2012). In some configurations, the polysaccharide can be a polysaccharide that can be subject to hydrolysis by an enzyme produced by colonic microflora such as, for example, a pectinase. In some configurations, a polysaccharide comprised by an inner coating can be a pectin or another polysaccharide substrate of colon enzymes.

In some configurations, an inner coating of the present teachings can comprise, consist essentially of, or consist of a polysaccharide. In some configurations, the polysaccharide can be a pharmaceutically acceptable polysaccharide, and can be a pectinase substrate, or another polysaccharide subject to digestion by enzyme(s) produced by colonic micro-flora (Nugent, S. G., et al., Gut 48: 571-577, 2001). In some configurations, the polysaccharide can be a pectin, xantham gum, locust bean gum, alginate, carrageenan, amylose, guar gum, inulin, dextran, chitosan, chondroitin sulfate or combinations thereof. In some configurations, the polysaccharide can be a pectin. In some configurations, the pectin can be a high methylester (HM) pectin. In an embodiment, said inner coating dissolves in about 60 minutes in aqueous medium. In an embodiment, said inner coating is not pH-dependent.

In an embodiment, said inner coating further comprises pharmaceutically acceptable excipients. In an embodiment, said excipients are chosen from plasticizers, anti-tacking agent, opacifiers, and combinations thereof. In an embodiment, said plasticizer is chosen from acetyl tributyl citrate, acetyl triethyl citrate, castor oil, diacetylate monoglycerides, dibutyl sebacate, diethyl phthalate, glycerin, glycerol, polyethylene glycols, polyethylene glycol monomethyl ether, polyvinylpyrrolidone, propylene glycol, sorbitol, sorbitan solution, triacetin, tributyl citrate, and triethyl citrate. In an embodiment, said anti-tacking agent is chosen from talc, glycerol monostearate, and colloidal silica. In an embodiment, said opacifier is titanium dioxide.

In various configurations, the weight of an inner coating of a particulate of the present teachings can be 1% relative to the weight of a core, about 1%, 2%, about 2%, 3%, about 3%, 4%, about 4%, 5%, about 5%, 6%, about 6%, 7%, about 7%, 8%, about 8%, 9%, about 9%, 10%, about 10%, 11%, about 11%, 12%, about 12%, 13%, about 13%, 14%, about 14%, 15% about 15%, 16%, about 16%, 17%, about 17%, 18%, about 18%, 19%, about 19%, 20%, or about 20% relative to the weight of a core. In an embodiment, the weight of the inner coating is present in an amount in a range of about 3% to 25% by weight relative to the weight of the core. In another embodiment, the weight of the inner coating is present in an amount in a range of about 3% to 7% by weight relative to the weight of the core. In another embodiment, the weight of the inner coating is present in an amount in a range of about 8% to 12% by weight relative to the weight of the core. In another embodiment, the weight of the inner coating is present in an amount in a range of about 13% to 17% by weight relative to the weight of the core. In another embodiment, the weight of the inner coating is present in an amount in a range of about 18% to 22% by weight relative to the weight of the core. In another embodiment, the weight of the inner coating is present in an amount of about 5% by weight relative to the weight of the core. In another embodiment, the weight of the inner coating is present in an amount of about 10% by weight relative to the weight of the core. In another embodiment, the weight of the inner coating is present in an amount of about 15% by weight relative to the weight of the core. In another embodiment, the weight of the inner coating is present in an amount of about 20% by weight relative to the weight of the core.

In another embodiment, the weight of the inner coating is present in an amount in a range of about 5% to 15% by weight relative to the weight of the core.

In another embodiment, the weight of the inner coating is present in an amount of about 5% by weight relative to the weight of the core.

In some configurations, an outer coating can comprise, consist essentially of, or consist of a polymer or a combination of polymers that is stable at low pH i.e., at pH<6.0, but can dissolve at a pH≥6.0. In various configurations, an outer coating can comprise, consist essentially of, or consist of a polymer that is stable in acidic conditions such as found in the stomach but can dissolve at a higher pH range such as a pH of the lumen of the colon. In various configurations, an outer coating of an oral composition of the present teachings can be stable at stomach pH and upper intestine luminal pH, but can dissolve at colon luminal pH in 30 minutes or less, about 30 minutes or less, 45 minutes or less, about 45 minutes or less, –60 minutes or less, or about 60 minutes or less.

In various configurations, an outer coating that can resist dissolution in a stomach environment but can dissolve in a colon environment can comprise, consist essentially of, or consist of a pharmaceutically acceptable, pH-sensitive polymer such as, without limitation, a polymethacrylate, a cellulose acetate phthalate (CAP), a cellulose acetate trimellitate (CAT), a hydroxypropylmethylcellulose phthalate (HPMCP) or a combination thereof.

In some configurations, a particulate of the present teachings can have an outer coating that is proportionally 3% of total particulate weight, about 3%, 4%, about 4%, 5%, about 5%, 6%, about 6%, 7%, about 7%, 8% about 8%, 9%, about 9%, 10%, about 10%, 11%, about 11%, 12%, about 12%, 13%, about 13%, 14%, about 14%, 15%, about 15%, 16%, about 16%, 17%, about 17%, 18%, about 18%, 19%, about 19%, 20%, about 20%, 21%, about 21%, 22%, about 22%, 23%, about 23%, 24%, about 24%, 25%, about 25%, 26%, about 26%, 27%, about 27%, 28%, about 28%, 29%, about 29%, 30%, or about 30% of total particulate weight. In an embodiment, the weight of the outer coating is present in an amount in a range of about 3% to 25% by weight relative to the weight of the inner coated core. In another embodiment, the weight of the outer coating is present in an amount in a range of about 3% to 7% by weight relative to the weight of the inner coated core. In another embodiment, the weight of the outer coating is present in an amount in a range of about 8% to 12% by weight relative to the weight of the inner coated core. In another embodiment, the weight of the outer coating is present in an amount in a range of about 13% to 17% by weight relative to the weight of the inner coated core. In another embodiment, the weight of the outer coating is present in an amount in a range of about 18% to 22% by weight relative to the weight of the inner coated core. In another embodiment, the weight of the outer coating is present in an amount of about 5% by weight relative to the weight of the inner coated core. In another embodiment, the weight of the outer coating is present in an amount of about 10% by weight relative to the weight of the inner coated core. In another embodiment, the weight of the outer coating is present in an amount of about 15% by weight relative to the weight of the inner coated core. In another embodiment, the weight of the outer coating is present in an amount of about 20% by weight relative to the weight of the inner coated core.

In another embodiment, the weight of the outer coating is present in an amount in a range of about 5% to 15% by weight relative to the weight of the inner coated core.

In another embodiment, the weight of the outer coating is present in an amount of about 10% by weight relative to the weight of the inner coated core.

In some configurations, a particulate in accordance with the present teachings can comprise an outer coating that can comprise, consist essentially of, or consist of a pharmaceutically acceptable, pH-sensitive polymer or a combination of two polymers such as, without limitation, a polymethacrylate. In various configurations, the polymethacrylate can be, for example and without limitation, a polymer such as poly(methyl acrylate-co-methyl methacrylate-co-methacrylic acid) 7:3:1 (e.g., EUDRAGIT® FS 30 D) (Evonik Corporation, Parsippany, N.J.), poly(methacrylic acid-co-methyl methacrylate) 1:1 (e.g., EUDRAGIT® L100), poly (methacrylic acid-co-methyl methacrylate) 1:2 (e.g., EUDRAGIT® S100), singly or in combination with poly (methacrylic acid-co-ethyl acrylate) 1:1 (e.g., EUDRAGIT® L 30 D-55).

In some configurations, an outer coating of a particulate of the present teachings can further comprise one or more pharmaceutically acceptable coating additives, such as, without limitation, an anti-tacking agent, a plasticizer, a stabilizer or a combination thereof. In various configurations, a coating additive can be, for example and without limitation, a PLASACRYL™ such as PLASACRYL™ T20 (Evonik Corporation, Parsippany, N.J.), triethyl citrate, acetyl tributyl citrate, acetyl triethyl citrate, diacetylated monoglycerides, dibutyl sebacate, diethyl phthalate, triacetin, tributyl citrate, glycerin, a polyethylene glycol, a polyethylene glycol monomethyl ether, a propylene glycol, sorbitol sorbitan, titanium dioxide, talc, glycerol monostearate, a polysorbate, or a combination thereof.

In some embodiments, a pharmaceutical dosage form of the present teachings can comprise a plurality of particulates, each particulate comprising a core comprising a pharmaceutical compound, a polysaccharide inner coating surrounding the core, and an outer coating comprising a polymer such as a polymethacrylate, a cellulose acetate phthalate (CAP), a cellulose acetate trimellitate (CAT), a hydroxypropylmethylcellulose phthalate (HPMCP) or a combination thereof, wherein the outer coating surrounds the inner coating. In some configurations, a shell can encapsulate a plurality of particulates.

In some configurations, a pharmaceutical dosage form of the present teachings can be a tablet which can comprise a plurality of particulates plus additional excipient material such as a binder, a colorant, a disintegrant, a lubricant, a glidant, a flavoring, a preservative, a diluent or a combination thereof.

In some configurations, a pharmaceutical dosage form of the present teachings can comprise a plurality of particulates and a shell encapsulating the plurality of particulates. In some configurations, a shell can comprise a pharmaceutically acceptable material such as, without limitation, a gelatin, a hydroxypropylmethyl cellulose or a combination thereof.

In some configurations, an oral composition of the present teachings such as a tablet or capsule can comprise a plurality of particulates, each particulate comprising an inner coating comprising a pharmaceutically acceptable polysaccharide. In some configurations, the polysaccharide can be a polysaccharide enzyme substrate or a pectinase substrate. In various configurations, the polysaccharide can be, such as but without limitation, a pectin, xantham gum, locust bean gum, alginate, carrageenan, a guar gum, an amylose, an inulin, a dextran, a chitosan, a chondroitin sulfate or a combination thereof. In various configurations, the polysaccharide can be a pectin. In some configurations, the pectin can be HM grade pectin.

In some configurations, the outer coating of a particulate of the present teachings can comprise a pharmaceutically acceptable polymer such as a polymethacrylate. In some configurations, the polymethacrylate can be poly(methyl acrylate-co-methyl methacrylate-co-methacrylic acid) 7:3:1 or a mixture comprising poly(methyl acrylate-co-methyl methacrylate-co-methacrylic acid) 7:3:1 and poly(methacrylic acid-co-methyl methacrylate) 1:1.

In some configurations, an oral composition of the present teachings can comprise an outer coating comprising one or more coating additives. In some configurations a coating additive can be an anti-tacking agent, a plasticizer and a stabilizer. In various configurations, a coating additive can be, without limitation, PLASACRYL™ (Evonik Corporation, Parsippany, N.J.), triethyl citrate, acetyl tributyl citrate, acetyl triethyl citrate, diacetylated monoglycerides, dibutyl sebacate, diethyl phthalate, triacetin, tributyl citrate, glycerin, polyethylene glycols, polyethylene glycol monomethyl ether, propylene glycol, sorbitol sorbitan, titanium dioxide, talc, glycerol monostearate, or a polysorbate.

In some configurations, an oral composition of the present teachings can comprise an outer coating that does not dissolve at a pH less than 6.0 and dissolves at pH≥6.0. In some configurations, the outer coating can dissolve at pH>6, pH 6.5, about pH 6.5, pH 7, about pH 7, pH 7.5 or about pH 7.5. In some configurations the outer coating does not dissolve at a pH≤6.0 in at least 120 minutes and dissolves at pH>7.0 in 30 minutes or less.

In an embodiment, the drug release at about pH 7.5 is greater than 85% in about 45 minutes wherein said inner coating is pectin.

It is known that each enteric coating has a specific pH at which it dissolves. It has been discovered herein that the combination of a polysaccharide enzyme substrate polymer inner coating and an enteric outer coating will cause a shift in the dissolution pH of the enteric coating. This allows for more specific on-site delivery of the API to the colon due to the higher pH found therein.

Said inner coated core, wherein said inner coating is pectin, dissolves at pH 7.0 in about 30 minutes. Similarly, the core coated only in the outer layer (lacking the inner pectin coating) dissolves at pH 7.0 in about 30 minutes. Unexpectedly, the drug release from the core with both the inner pectin coating and outer coating is only about 10% at pH 7.0 in about 30 minutes, and it requires a higher pH of 7.4 to dissolve greater than 85% in about 45 minutes.

Said inner coated core, wherein said inner coating is pectin, dissolves at pH 6.0 in about 30 minutes. Similarly, the core coated only in the outer layer (lacking the inner pectin coating) dissolves at pH 6.0 in about 30 minutes. Unexpectedly, at a higher pH of about pH 6.5, the drug release from the core with both the inner pectin coating and outer coating is greater than 85% in about 30-60 minutes.

Said inner coated core, wherein said inner coating is pectin, dissolves at pH 6.0 in about 30 minutes. Similarly, the core coated only in the outer layer (lacking the inner pectin coating) dissolves at pH 6.0 in about 30 minutes. Unexpectedly, at a higher pH of about pH 6.5, the drug release from the core with both the inner pectin coating and outer coating is greater than 85% in about 30 minutes.

Said inner coated core, wherein said inner coating is pectin, dissolves at pH 6.0 in about 30 minutes. Similarly, the core coated only in the outer layer (lacking the inner pectin coating) dissolves at pH 6.0 in about 30 minutes. Unexpectedly, at a higher pH of about pH 6.5, the drug release from the core with both the inner pectin coating and outer coating is greater than 85% in about 45 minutes.

Said inner coated core, wherein said inner coating is pectin, dissolves at pH 6.0 in about 30 minutes. Similarly, the core coated only in the outer layer (lacking the inner pectin coating) dissolves at pH 6.0 in about 30 minutes. Unexpectedly, at a higher pH of about pH 6.5, the drug release from the core with both the inner pectin coating and outer coating is greater than 85% in about 60 minutes.

In some configurations, a particulate of an oral composition of the present teachings can further comprise an excipient such as, but without limitation, microcrystalline cellulose, hydroxypropyl cellulose, croscarmellose sodium, magnesium stearate or a combination thereof. In various configurations, a particulate can comprise about 15% microcrystalline cellulose, about 5% hydroxypropyl cellulose, about 3% croscarmellose sodium and about 0.3% magnesium stearate.

In some embodiments, an oral composition of the present teachings can be a capsule comprising a plurality of particulates, and a capsule shell. In various configurations, each particulate can comprise a core comprising a pharmaceutical compound, a pectinase-sensitive inner coating surrounding the core, and an outer coating comprising a polymer selected from the group consisting of a polymethacrylate, cellulose acetate phthalate (CAP), a cellulose acetate trimellitate (CAT), a hydroxypropylmethylcellulose phthalate (HP-MCP) and a combination thereof, wherein the outer coating encapsulates the inner coating. In some configurations, the total amount of the pharmaceutical compound in a capsule can be from 50 to 800 mg metronidazole, such as, for example, 125, 250, 500 or 750 mg metronidazole. In some configurations, each particulate can further comprise one or more excipients such as, without limitation, microcrystalline cellulose, hydroxypropyl cellulose, croscarmellose sodium and magnesium stearate. In some configurations, the inner coating can comprise pectin, and can further comprise titanium dioxide.

DETAILED DESCRIPTION

The present teachings include descriptions that are not intended to limit the scope of any claim. The examples and methods are provided to further illustrate the present teachings. Those of skill in the art, in light of the present disclosure, will appreciate that many changes can be made in the specific embodiments that are disclosed and still obtain a like or similar result without departing from the spirit and scope of the present teachings. As used herein, the singular forms "a", "an" and "the" are intended to include the plural forms as well, unless the context indicates otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "inner coated core" as used herein describes the core coated with only the polysaccharide inner coating surrounding it.

The terms "dissolve" and "complete release" as used herein is describe a scenario when at least 85% of the component being described has dissolved. With respect to the core, the term "dissolve" means that at least 85% of the drug has been released.

Methods and compositions described herein utilize laboratory techniques well known to skilled artisans. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996, Augsburger, L. L. et al. Pharmaceutical Dosage Forms—Tablets, CRC Press, 2008, Thakur, V. K., et al. Handbook of Polymers for Pharmaceutical Technologies, Biodegradable Polymers, John Wiley & Sons, 2015 and Rowe, R. C., et al., Handbook of Pharmaceutical Excipients, Pharmaceutical Press, 2012. All publications cited herein are incorporated by reference, each in its entirety.

Figure 1:
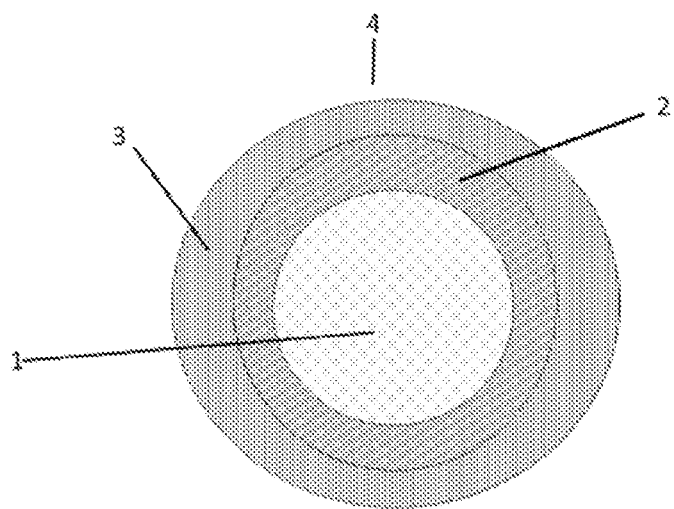
FIG. 1 is a schematic diagram of a particulate of the present teachings.

As shown in FIG. 1, a particulate (4) of the present teachings can comprise, consist essentially of or consist of a core (1) which is surrounded by an inner coating (2) which comprises, consists of, or consists essentially of a polysaccharide, and an outer coating (3) surrounding the inner coating, which comprises, consists essentially of, or consists of a pH-dependent polymer. Additional coatings or layers, such as, but without limitation, cosmetic coatings or non-functional coatings, can also separate any of the layers or be used to further coat a complete particulate.

Figure 2:
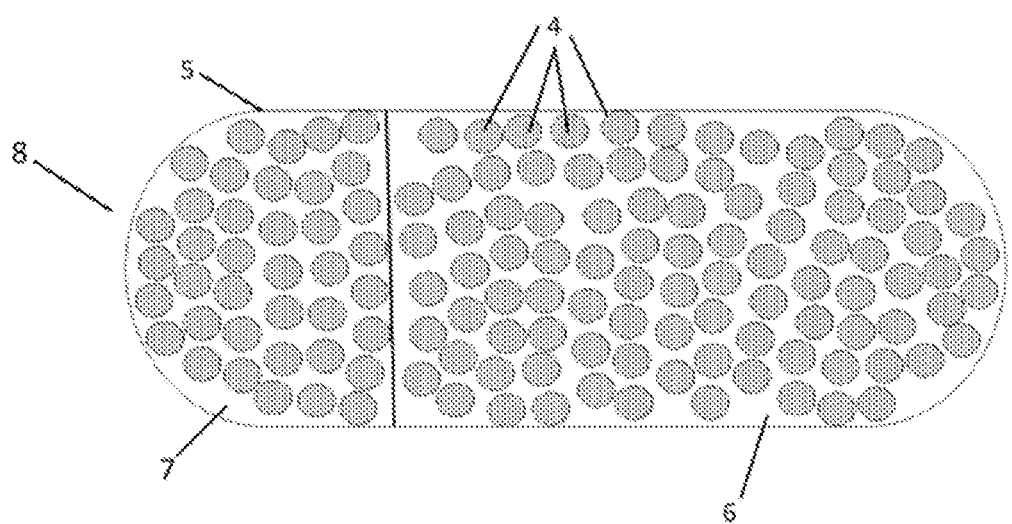
FIG. 2 is a schematic diagram of a capsule filled with particulates of the present teachings.
Figure 3:
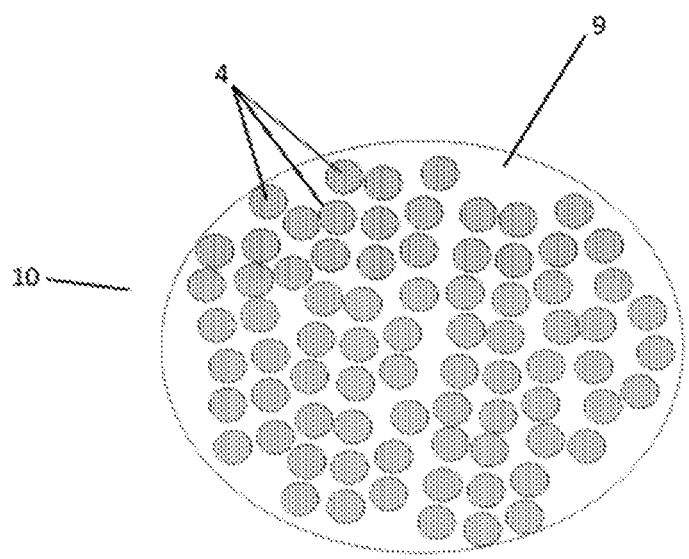
FIG. 3 is a schematic diagram of a tablet pressed from particulates of the present teachings and an excipient.

A plurality of particulates of the present teachings can comprise a single oral dosage form, or can be part of a multiparticulate that is packaged into a larger oral dosage form. As illustrated in FIG. 2, a gelatinous capsule shell (5) can contain a plurality of particulates (4). A capsule (8) can include a body (6) and a cap (7). Upon oral administration, a gelatinous capsule shell can dissolve in the stomach and the plurality of particulates can then proceed to the colon. Alternately, as shown in FIG. 3, a plurality of particulates (4) can be combined with one or more excipients (9) and pressed into a tablet (10). In various configurations, a tablet can be further coated with a coating, such as, without limitation, a cosmetic coating.

As used herein, a "particulate" can be a bead, a pellet, or a mini-tablet, and can be a portion of a larger dosage form. A particulate, bead, pellet, or mini-tablet comprises a core, an inner coating, and an outer coating in accordance with the present teachings.

In various configurations, a particulate can be, without limitation, spherical or cylindrical in shape. In some configurations, a particulate can comprise from 3-10 mg of a pharmaceutical compound such as, for example, metronidazole. In some configurations, a particulate can have a diameter of from about 1 mm up to about 3 mm. In various configurations, the total weight of a particulate can range from about 1 mg up to about 25 mg.

In various configurations, a dosage form can be comprised of a plurality of particulates. A dosage form comprising a plurality of particulates can have, for example, from 50 mg-800 mg. In an embodiment, said dosage form comprises 500 mg of metronidazole. In an embodiment, said dosage form comprises 250 mg of metronidazole.

As used herein, a core comprises a pharmaceutically active substance, and can further comprise one or more excipients in accordance with the present teachings.

As used herein, an inner coating comprises a polysaccharide that is sensitive to digestion by enzymes present in the lumen of the colon, in particular hydrolases harbored by colonic microflora. An inner coating can further comprise coating additives in accordance with the present teachings.

As used herein, an outer coating comprises a pH-dependent polymer that is stable at pH<6.0, but dissolves at pH≥6.0.

Polysaccharides of the present teachings include polysaccharide enzyme substrate polymers that are subject to hydrolysis by enzymes of colonic microorganisms. Polysaccharides of the present teachings include, but are not limited to, amylose, xantham gum, locust bean gum, alginate, carrageenan, arabinoga lactose, chitosan, cyclodextrins, chondroitin sulfate, pectin, dextran, guar gum, xylan and inulin.

Pectins are anionic polysaccharides extracted from plant primary cell walls. Pharmaceutical grade pectin is available under a variety of tradenames, e.g., GENU® (CP Kelco, Atlanta, Ga.) and Grindsted® (Dupont Nutrition & Health). Pectin is commercially available in three grades depending on the degree of esterification: high methylester (HM), conventional low methylester pectin (LMC), and low methylester amidated (LMA).

Outer coating. As used herein, an outer coating is a pH-dependent enteric coating that is stable at pH 1-6 (stomach) but dissolves at pH>6 (i.e., at a pH range found in the lumen of the colon). pH-dependent coatings can include, without limitation, a polymethacrylate, a cellulose acetate phthalate (CAP), a cellulose acetate trimellitate (CAT), a hydroxypropylmethylcellulose phthalate (HPMCP), polyvinyl acetate phthalate (COATERIC™, Colorcon Ltd., Harleysville, Pa.), polyvinyl acetate phthalate (SURETERIC™ Colorcon, Ltd.), and cellulose acetate phthalate (AQUATERIC™, FMC Corp., Philadelphia, Pa.)

Hydroxypropylmethylcellulose phthalate. Hydroxypropylmethylcellulose phthalate is available in several grades under different tradenames, such as, without limitation, hydroxypropyl methylcellulose phthalate HP50 (HPMCP-HP50) (USP/N F 220824), HP55 (HPMCP-HP55) (USP/NF type 200731) and HP55S (Shin Etsu Chemical, Tokyo, Japan).

Polymethacrylate. Polymethacrylates include polymers that can be used in pharmaceutical coatings. Polymethacrylates are available under several trade names such as, for example and without limitation, EUDRAGIT® (Evonik Corporation, Parsippany, N.J.). Several polymethacrylates available under the tradename EUDRAGIT® can be used in a particulate of the present teachings, such as and without limitation, poly(methacrylic acid-co-ethyl acrylate) 1:1 (L 30 D-55, L 100-55), poly(methacrylic acid-co-methyl methacrylate) 1:1 (L100, L 12.5), poly(methacrylic acid-co-methyl methacrylate) 1:2 (S100, S 12.5), and poly(methyl acrylate-co-methyl methacrylate-co-methacrylic acid) 7:3:1 (FS 30 D). Poly(methyl acrylate-co-methyl methacrylate-co-methacrylic acid) 7:3:1 is available in a 30% aqueous dispersion under the trade name EUDRAGIT® FS 30 D and dissolves at pH 7.0. Poly(methacrylic acid-co-ethyl acrylate) 1:1 is available as a 30% aqueous dispersion under the trade name EUDRAGIT® L-30-D-55 and dissolves at pH 5.5. Combinations of two polymethacrylates can be used to form coatings that dissolve at different pH levels; the relative amounts of polymethacrylates as well as coating additives can be adjusted to modify the pH stability of a coating.

Coating additives. A variety of materials can be added to the inner coating or the outer coating, such as a stabilizer, a plasticizer, and/or an anti-tacking agent. In some configurations, a stabilizer can be an emulsifier such as, for example, polysorbate 80. In some configurations, a plasticizer can be, for example, acetyl tributyl citrate, acetyl triethyl citrate, castor oil, diacetylate monoglycerides, dibutyl sebacate, diethyl phthalate, glycerin, glycerol, polyethylene glycols, polyethylene glycol monomethyl ether, polyvinylpyrrolidone, propylene glycol, sorbitol, sorbitan solution, triacetin, tributyl citrate, and triethyl citrate. In some configuration, an anti-tacking agent can be, for example, colloidal silicon dioxide, fumed silica, glycerol monostearate (GMS), magnesium stearate or talc. Commercially available coating additives can contain any of the foregoing types of coating additives in combination. For example, and without limitation, additives available under the tradename PLASACRYL™ (Evonik Corporation, Parsippany, N.J.), which contains a stabilizer, a plasticizer and an anti-tacking agent. PLASACRYL™ T20 can be used with polymethacrylates EUDRAGIT® FS 30 D and EUDRAGIT® L-30-D-55 (Evonik Corporation, Parsippany, N.J.). Other coating additives can include an opacifier or pigment, such as and without limitation, titanium dioxide.

Excipients. Non-limiting examples of excipients include microcrystalline cellulose, polyvinylpyrrolidone, hydroxypropylcellulose. Polyvinylpyrrolidone is available under several different grades, such as, for example and without limitation, K15, K25, K30, and K90. Hydroxypropylcellulose is available from various suppliers under a variety of trade names, such as KLUCEL™ (Ashland Inc., Covington, Ky.) HF Pharm, HXF Pharm, MF Pharm, MXF Pharm, GF Pharm, GXF Pharm, JF Pharm, JXF Pharm, LF Pharm, JXF Pharm, LF Pharm, LXF Pharm, EF Pharm, EXF Pharm, ELP Pharm; Nisso HPC (Nisso America Inc., New York, N.Y.) SSL, SL, L, and M.

Diluents. Non-limiting examples of diluents include microcrystalline cellulose, lactose monohydrate, lactose anhydrous, a starch such as maize starch, wheat starch, potato starch, or pregelatinized starch, a sugar such as sorbitol, mannitol, maltitol, xylitol, dextrose, sucrose, or fructose, kaolin, calcium phosphate, calcium sulfate, and calcium carbonate. Non-limiting examples of microcrystalline cellulose include AVICEL® PH-101, PH-102, PH-103, PH-105, pH-112, PH-113, PH-200, PH-301 and PH-302 (FMC Corporation, Philadelphia, Pa.); PHARMACEL® 101, 102, and 112 (DFB Pharma, Paramus, N.J.); and GRINDSTED® (Danisco, Madison, Wis.).

Binders. Non-limiting examples of binders include microcrystalline cellulose, hydroxypropyl cellulose, such as KLUCEL™ (Ashland Inc., Covington, Ky.) HF, HXF, MF, MXF, GF, GXF, JF, JXF, LF, JXF, LF, LXF, EF, EXF, ELP, hydroxypropyl methylcellulose (HPMC), polyvinylpyrrolidone, sodium carboxymethylcellulose, sucrose, liquid glucose, acacia, tragacanth, gelatin, starch paste, pregelatinized starch, alginic acid, cellulose, methyl cellulose, ethyl cellulose potassium alginate and sodium alginate.

Disintegrants. Non-limiting examples of disintegrants include pregelatinized starch, microcrystalline cellulose, croscarmellose sodium, crospovidone, and sodium starch glycolate.

Lubricants. Non-limiting examples of lubricants include magnesium stearate, calcium stearate, stearic acid, hydrogenated vegetable oil, mineral oil, polyethylene glycol, sodium lauryl sulfate, glycerol palmitostearate, glyceryl behenate, sodium benzoate, and sodium stearyl fumarate.

Glidant. Non-limiting examples of glidants include colloidal silicon dioxide, silicon dioxide and talc.

EXAMPLES

General Manufacturing Procedure

The following process was used to prepare core particulates, inner and outer coating, having compositions defined in Example 1.

API (with particle size suitable for direct compression), diluent (such as microcrystalline cellulose and/or lactose), disintegrant (such as sodium starch glycolate, Crospovidone, or Croscarmellose sodium), and binder (such as Povidone K30 or Hydroxypropyl cellulose EXF) were dry-blended for 5 minutes, then blended with lubricant (such as Magnesium stearate) for 3 minutes, then compressed on rotary tablet press with multi-tip tooling with diameter of 2 mm, into min-tablets.

API (with fine particle size), diluent (such as microcrystalline cellulose and/or lactose), and disintegrant (such as sodium starch glycolate, Crospovidone, or Croscarmellose sodium) were blended in a high-shear granulator for 3 minutes, granulated with binder (such as Povidone K30 or Hydroxypropyl cellulose EXF) water solution, then 1) dried in a fluid bed dryer at 60° C. until a moisture of <3%, then milled and compressed on rotary tablet press with multi-tip tooling with diameter of 2 mm, into min-tablets; or 2) extruded and spheronized into pellets of about 1-3 mm, and then dried in a fluid bed dryer at 60° C. until a moisture of <3%.

The mini-tablets or pellets were coated with inner and outer coating dispersion on a perforated coater or a bottom spray fluid bed coater at exhaust temperature of 40-50° C. for the inner coating and 30-35° C. for the outer coating.

Example 1

This example illustrates the preparation of uncoated cores of the present teachings.

| Ingredient | Core 1 mg/dose | % | Core 2 mg/dose | % | Core 3 mg/dose | % | Core 4 mg/dose | % | Core 5 mg/dose | % |
|---|---|---|---|---|---|---|---|---|---|---|
| Metronidazole | 125 | 50.2 | 250 | 68.1 | 375 | 57.0 | 500 | 76.3 | 500 | 75.5 |
| Microcrystalline cellulose (PH101) | | | 75 | 20.4 | 250 | 38.0 | | | | |
| Microcrystalline cellulose (PH102) | 50 | 20.1 | | | | | 100 | 15.3 | 100 | 15.1 |
| Lactose monohydrate | 50 | 20.1 | | | | | | | | |
| Polyvinylpyrrolidone (Povidone K30) | 15 | 6.0 | 20 | 5.4 | | | | | | |
| Hydroxypropyl cellulose (EXF) | | | | | 30 | 4.6 | 33 | 5.0 | 40 | 6.0 |
| Sodium starch glycolate | | | 20 | 5.4 | | | | | 20 | 3.0 |
| Crospovidone | 8 | 3.2 | | | | | | | | |
| Croscarmellose sodium | | | | | | | 20 | 3.1 | | |
| Magnesium stearate | 1 | 0.4 | 2 | 0.5 | 3 | 0.5 | 2 | 0.3 | 2 | 0.3 |
| Total Weight | 249 | 100 | 367 | 100 | 658 | 100 | 655 | 100 | 662 | 100 |

Example 2

This example illustrates the inner and outer coatings suitable for the cores described herein.

| Ingredient | Formula 1 mg/dose | % WG | Formula 2 mg/dose | % WG | Formula 3 mg/dose | % WG | Formula 4 mg/dose | % WG | Formula 5 mg/dose | % WG |
|---|---|---|---|---|---|---|---|---|---|---|
| Core Weight | 655 (core 4) | | 655 (core 4) | | 367 (core 2) | | 367 (core 2) | | 655 (core 4) | |
| Inner Coating | | | | | | | | | | |
| HPMC (Spectrablend ™ White) | 30 | | | | | | | | | |
| Pectin (HM) | | | 25 | | | | 36.7 | | 45 | |
| Guar gum | | | | | 30 | | | | | |
| Glycerin | | | 5 | | 9 | | | | 5 | |
| Titanium dioxide | | | 2.5 | | | | | | | |
| Talc | | | | | 5 | | | | 15 | |
| Inner Coating Total Weight | 30 | 4.6 | 32.5 | 5.0 | 44 | 12.0 | 36.7 | 10.0 | 65 | 10.0 |
| Outer Coating | | | | | | | | | | |
| Eudragit FS 30D | 63 | | 63 | | 22 | | 40 | | 130 | |
| Eudragit L 30D-55 | | | | | 3.6 | | 2 | | | |
| Eudragit S100 | | | | | | | | | | |

-continued

|  | Formula 1 | | Formula 2 | | Formula 3 | | Formula 4 | | Formula 5 | |
| --- | --- | --- | --- | --- | --- | --- | --- | --- | --- | --- |
| Ingredient | mg/dose | % WG | mg/dose | % WG | mg/dose | % WG | mg/dose | % WG | mg/dose | % WG |
| PlasAcryl T20 | 6.3 | | 6.3 | | | | | | | |
| Polysorbate 80 | | | | | | | | | 2.1 | |
| Triethyl citrate | | | | | 1.8 | | | | 6.5 | |
| Glycerol monostearate | | | | | | | | | 5.2 | |
| Talc | | | | | 13.8 | | 20 | | | |
| Total Weight | 69.3 | 10 | 69.3 | 10 | 41.2 | 10 | 62 | 15 | 143.8 | 20 |

Example 3

This example illustrates dissolution testing of examples described herein. Dissolution conditions are as follows: USP apparatus II—Paddle method at 75 rpm, 900 mL medium, at 37° C.

Figure 4:
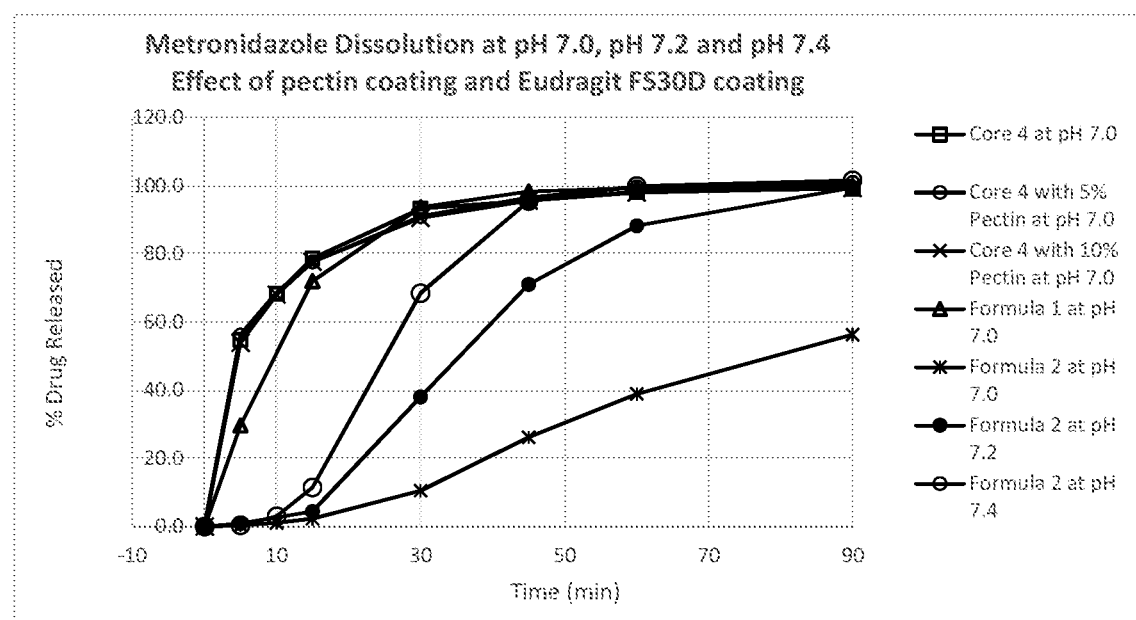
FIG. 4 illustrates dissolution testing at pH 7.0, 7.2, and pH 7.4 using the paddle method at 75 rpm, 900 mL of medium at 37° C. Data for Core 4 alone, Core 4 with varying degrees of pectin inner coating (and no outer coating), and Formulas 1 and 2 are shown.

The effect that the inner coating alone, outer coating alone and in conjunction with the outer coating is shown in FIG. 4. Metronidazole mini-tablet core showed immediate and complete release (>85%) in 30 minutes. Both the 5% and 10% pectin coatings did not have a substantial change on the dissolution profile. When a Eudragit FS 30D outer coating is added, without pectin as the inner coating, but using a non-functional HPMC-based seal coating in the place of pectin, produced fast release at pH 7.0, slightly slower than the core, but still showed a complete release at 30 minutes. The dissolution profile is similar to the non-enterically coated inner coated cores and non-coated cores. Only when the pectin inner coating and Eudragit FS30D outer layer combination showed an improved effect on drug dissolution retardation. At a higher pH of 7.4, the drug release was increased to a complete release (>85%) at 45 minutes.

Figure 5:
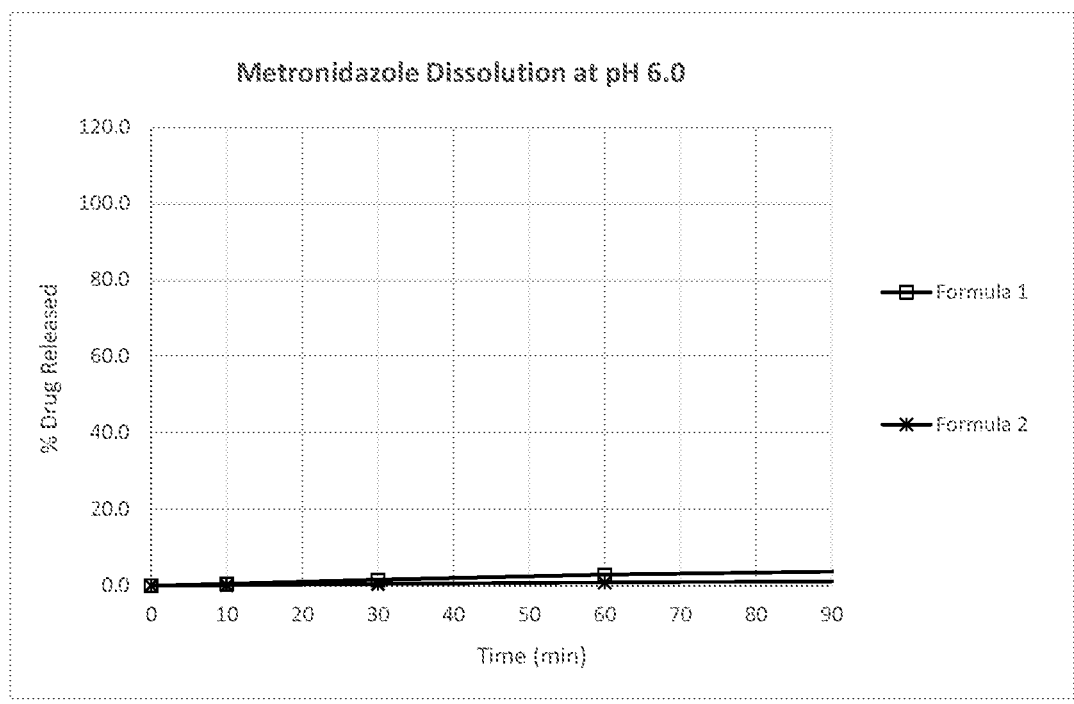
FIG. 5 illustrates dissolution profiles at pH 6.0, using the paddle method at 75 rpm, 900 mL of medium at 37° C. for Formulas 1 and 2.

The dissolution profile for Formulas 1 and 2 at pH 6.0 is shown in FIG. 5. At pH 6.0, regardless the existence of pectin inner coating, Eudragit FS30D coated cores demonstrated release of no more than 5%.

Figure 6:
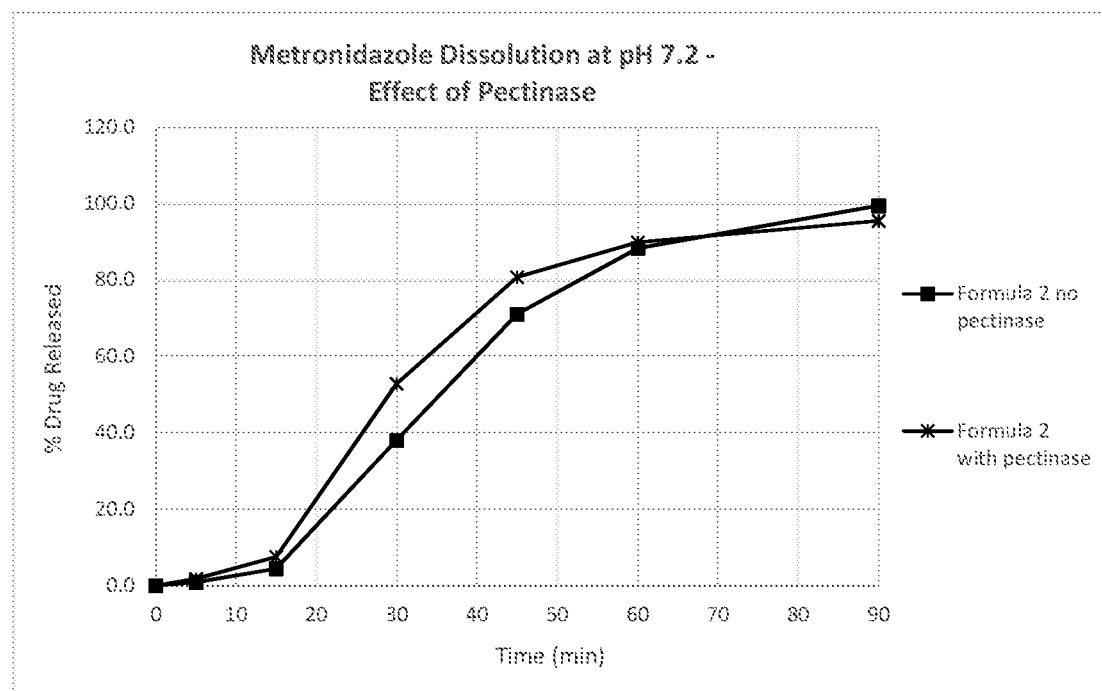
FIG. 6 illustrates dissolution profiles at pH 7.2, using the paddle method at 75 rpm, 900 mL of medium at 37° C., shows the effects of pectinase on dissolution.

The effect of pectinase in the dissolution media for Formula 2 is shown in FIG. 6. Since Formula 2 uses pectin as the inner coating, the presence of colon enzymes may have an effect on dissolution. At pectinase concentration of 1.1% v/v, metronidazole dissolution was increased 40% in 30 minutes, compared to dissolution in the same pH 7.2 buffer.

Animal testing is planned to study colon X-ray imaging of the coated mini-tablets in the dog model. Barium sulfate will be used as the contrast agent inside the core. After oral administration, X-ray images at different transit time will be taken for visual proof of dosage transit to the colon. Optimized and drug-loaded formulation will be tested for drug plasma profile and fecal drug concentration in human for oral drug bioavailability and drug concentration in feces to prove drug colon-specific delivery.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical minitablet comprising:
   a. a core comprising metronidazole and one or more pharmaceutically acceptable excipients selected from the group consisting of a diluent, a binder, a disintegrant, a lubricant, a glidant or a combination thereof wherein the core is formulated for immediate release;
   b. an inner coating surrounding the core comprising pectin and optionally at least one or more pharmaceutically acceptable excipients wherein the inner coating comprises at last 3 wt % relative to the weight of the core; and
   c. an outer coating surrounding the inner coating comprising a poly(methyl acrylate-co-methyl methacrylate-co-methacrylic acid) 7:3:1 wherein the outer coating comprises at least 10 wt % relative to the weight of the inner coated core wherein the minitablet has a diameter of about 1 mm to about 3 mm and (i) the inner coated minitablet without the outer coating dissolves in about 60 minutes or less in an aqueous media; (ii) the outer coating does not dissolve at pH<6.0; and (iii) greater than 85% of the metronidazole is released from the minitablet coated with the inner and outer coating in about 45 minutes when tested using a United States Pharmacopeia (USP) paddle method at 75 rpm and 900 mL of a medium with a pH of about 7.5.

2. The minitablet as recited in claim 1, wherein the outer coating further comprises a second polymethacrylate selected from the group consisting of poly(methacrylic acid-co-methyl methacrylate) 1:1, poly(methacrylic acid-co-methyl methacrylate) 1:2, poly(methacrylic acid-co-ethyl acrylate) 1:1, and a combination thereof.

3. A pharmaceutical dosage form comprising:
a plurality of minitablets as recited in claim 1.

4. The minitablet as recited in claim 1, wherein the weight of the inner coating is present in an amount in a range of about 3% to 25% by weight relative to the weight of the core.

5. The minitablet as recited in claim 4, wherein the weight of the inner coating is present in an amount of about 5-10% by weight relative to the weight of the core.

6. The minitablet as recited in claim 1, wherein the weight of the outer coating is present in an amount in a range of about 5% to 25% by weight relative to the weight of the core.

7. The minitablet as recited in claim 6, wherein the weight of the inner coating is present in an amount of about 10% by weight relative to the weight of the core.

8. A method of treating a colon disease comprising administering to a subject in need thereof a pharmaceutical dosage form comprising a plurality of minitablets as recited in claim 1.

9. The method as recited in claim 8, wherein said colon disease is chosen from colon cancer and an inflammatory bowel disease.

10. The method as recited in claim 9, wherein said inflammatory bowel disease is chosen from *C. difficile* infection, ulcerative colitis, or Crohn's disease.

11. The method as recited in claim 9, wherein said inflammatory bowel disease is *C. difficile* infection.

12. The method as recited in claim 8, wherein said administration is for 10-14 days.

13. The minitablet as recited in claim 1 wherein not more than about 5% of the metronidazole is release from the minitablet coated with the inner and outer coating in 90 minutes when tested using a USP paddle method at 75 rpm and 900 ml of a medium with a pH of 6.0.

14. A minitablet consisting of:
 (a) a core comprising (i) metronidazole and (ii) an excipient selected from the group consisting of a diluent, a binder, a disintegrant, a lubricant, a glidant or a combination thereof;
 (b) an inner coating layer surrounding the core comprising pectin and optionally at least one excipient;
 (c) an outer coating surrounding the inner coating comprising at least 10 wt % relative to the weight of the inner coated core and comprising a poly(methyl acrylate-co-methyl methacrylate-co-methacrylic acid) 7:3:1 and
 (d) optionally one or more cosmetic coatings or non-functional coatings applied to (a) the core; (b) the inner coating and/or (c) the outer coating;

wherein the minitablet has a diameter of about 1 mm to about 3 mm and (i) the inner coated minitablet without the outer coating dissolves in about 60 minutes or less in an aqueous media; (ii) the outer coating does not dissolve at pH≤6.0; and (iii) greater than 85% of the metronidazole is released from the minitablet coated with the inner and outer coating in about 45 minutes when tested using a United States Pharmacopeia (USP) paddle method at 75 rpm and 900 mL of a medium with a pH of about 7.5.

15. The minitablet of claim 14 wherein the outer coating further comprises a second polymethacrylate selected from the group consisting of poly(methacrylic acid-co-methyl methacrylate) 1:1, poly(methacrylic acid-co-methyl methacrylate) 1:2, poly(methacrylic acid-co-ethyl acrylate) 1:1, and a combination thereof.

16. A pharmaceutical dosage form comprising a plurality of minitablets as claimed in claim 14.

17. The minitablet as recited in claim 14 wherein not more than about 5% of the metronidazole is release from the minitablet coated with the inner and outer coating in 90 minutes when tested using a USP paddle method at 75 rpm and 900 ml of a medium with a pH of 6.0.

\* \* \* \* \*